(12) United States Patent
Molinari et al.

(10) Patent No.: US 6,719,975 B1
(45) Date of Patent: Apr. 13, 2004

(54) ANTI-HIRUDIN POLYCLONAL ANTIBODIES AND THEIR USE FOR THE IDENTIFICATION, IMMUNOPURIFICATION AND QUANTITATIVE DETERMINATION OF HIRUDIN

(75) Inventors: Antonio Molinari, Milan (IT); Marco Gerna, Milan (IT); Carla Giorgetti, Stradella (IT); Jacqueline Lansen, San Vittore Olona (IT); Romeo Roncucci, Milan (IT)

(73) Assignee: Farmitalia Carlo Erba S.r.l., Milan (IT)

( * ) Notice: Subject to any disclaimer, the term of this patent is extended or adjusted under 35 U.S.C. 154(b) by 1667 days.

(21) Appl. No.: 08/603,182

(22) Filed: Feb. 20, 1996

Related U.S. Application Data (63) Continuation of application No. 08/205,764, filed on Mar. 4, 1994, now abandoned, which is a continuation of application No. 07/903,797, filed on Jun. 24, 1992, now abandoned.

(30) Foreign Application Priority Data

Jun. 27, 1991 (IT) .......................................... MI91A1767

(51) Int. Cl.$^7$ ...................... A61K 39/00; G01N 33/531; C07K 16/38
(52) U.S. Cl. ................................. 424/191.1; 424/139.1; 424/151.1; 424/185.1; 424/194.1; 424/265.1; 435/70.21; 435/452; 435/331; 435/345; 436/543; 436/547; 436/548; 530/389.8; 530/855
(58) Field of Search ........................... 424/139.1, 151.1, 424/185.1, 191.1, 194.1, 265.1; 435/7.94, 69.3, 40.21, 452, 331, 345; 436/547, 548, 543; 530/324, 413, 806, 855, 389.8

(56) References Cited

U.S. PATENT DOCUMENTS 5,114,922 A * 5/1992 Maschler et al. .............. 514/12
5,272,059 A * 12/1993 Schlaeppi et al. ........ 435/70.21

FOREIGN PATENT DOCUMENTS

| EP | 0 074 248 | 3/1983 |
| EP | 0 380 443 | 8/1990 |

OTHER PUBLICATIONS

Schlaeppi, Jun. 01, 1991. Preparation of Monoclonal Antibodies to the Thrombin/Hirudin Complex. Thrombosis Res. 62: 459–70.*
Man et al., 1989, Treatment of Human Muscle Creatine Kinase With Glutaraldehyde Preferentially Increases the Immunogenicity . . . J Immunological Meth. 125: 251–9.*
Reichlin et al., 1970. Immunological Activity of Cytochrome c. J Biological Chem. 245: 947–954.*
de Taxis du Poet et al, 1991. Production of the HV1 Variant of Hirudin by Recombinant DNA Methodology. Blood Coagulation and Fibrinolysis 2: 113–20.*
Dodt et al, 1986. Expression, Secretion, and Processing of Hirudin in *E. coli* Using the Alkaline Phosphatase Signal Sequence. FEBS Lett. 202: 373–7.*
Harvey et al, 1986. Cloning and Expression of a cDNA Coding for the Anticoagulant Hirudin From the Bloodsucking Leech, *Hirudo medicinalis*. PNAS 83: 1084–8.*
Fortkamp et al, 1986. Cloning and Expression in *Escherichia coli* of a Synthetic DNA for Hirudin, the Blood Coagulation Inhibitor in the Leech. DNA 5: 511–17.*
Schlaeppi et al, Mar. 1990. Preparation of Monoclonal Antibodies to Hirudin and Hirudin Peptides. Eur. J. Biochem 188(2): 463–470.*
Spinner et al, 1986. Quantitative Enzyme–Linked Immunosorbent Assay (ELISA) for Hirudin. J. Immunol. Meth. 87: 79–83.*
Maurer et al, 1980. Proteins and Polypeptides as Antigens. Methods in Enzymol. 70: 49–70.*
Chemical Abstracts, vol. 98, No. 3, Jan. 17, 1983, p. 390.

* cited by examiner

*Primary Examiner*—James Grun
(74) *Attorney, Agent, or Firm*—Arent Fox Kintner Plotkin & Kahn

(57) ABSTRACT

A method of making antibodies to hirudin by immunizing with an immunogenic composition containing polymerized hirudin monomers in the absence of carrier protein is taught.

5 Claims, 4 Drawing Sheets

Figure 1. 15% polyacrylamide gel electrophoresis.
A: hirudin (20µg)
B: polymers obtained after reaction with glutaraldehyde (20µg)

Figure 2. Immunodiffusion in agarose gel according to Ouchterlony.
A: immune serum diluted 1:16
B: buffer
C, D, E: 2.5, 5 and 10μg of hirudin

Figure 3
Standard curve of HV1 hirudin in buffer, plasma and urine. The mean values of absorbance at 405 nm of 5 measurements with respective standard deviations are represented.

Figure 4

Specificity of anti-hirudin antibodies.

The IgGs recognize natural HV1 hirudin, recombinant HV2 hirudin but not FCE 27489.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (xi) SEQUENCE DESCRIPTION: SEQ ID NO:1:

Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
                35                  40                  45

Gln Ser His Asn Asp Gly Asp Phe Glu Glu Ile Pro Glu Glu Tyr Leu
    50                  55                  60

Gln
 65

(2) INFORMATION FOR SEQ ID NO:2:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (xi) SEQUENCE DESCRIPTION: SEQ ID NO:2:

Ile Thr Tyr Thr Asp Cys Thr Glu Ser Gly Gln Asn Leu Cys Leu Cys
1               5                   10                  15

Glu Gly Ser Asn Val Cys Gly Lys Gly Asn Lys Cys Ile Leu Gly Ser
                20                  25                  30

Asn Gly Lys Gly Asn Gln Cys Val Thr Gly Glu Gly Thr Pro Asn Pro
                35                  40                  45

Glu Ser His Asn Asn Gly Asp Phe Glu Glu Ile Pro Glu Glu Tyr Leu
    50                  55                  60

Gln
65

(2) INFORMATION FOR SEQ ID NO:3:

(i) SEQUENCE CHARACTERISTICS:
        (A) LENGTH: 65 amino acids
        (B) TYPE: amino acid
        (D) TOPOLOGY: linear     (ii) MOLECULE TYPE: peptide     (xi) SEQUENCE DESCRIPTION: SEQ ID NO:3:

```
Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Gln Gly Lys Asp Asn Gln Cys Val Thr Gly Glu Gly Thr Pro Lys Pro
        35                  40                  45

Gln Ser His Asn Gln Gly Asp Phe Glu Pro Ile Pro Glu Asp Ala Asp
    50                  55                  60

Glu
65
```

(2) INFORMATION FOR SEQ ID NO:4:

(i) SEQUENCE CHARACTERISTICS:
        (A) LENGTH: 64 amino acids
        (B) TYPE: amino acid
        (C) STRANDEDNESS: single
        (D) TOPOLOGY: linear     (ii) MOLECULE TYPE: peptide     (vi) ORIGINAL SOURCE:
        (A) ORGANISM: Hirudunaria manillensis     (xi) SEQUENCE DESCRIPTION: SEQ ID NO:4:

```
Val Ser Tyr Thr Asp Cys Thr Glu Ser Gly Gln Asn Tyr Cys Leu Cys
1               5                   10                  15

Val Gly Gly Asn Leu Cys Gly Gly Lys His Cys Glu Met Asp Gly
            20                  25                  30

Ser Gly Asn Lys Cys Val Asp Gly Glu Gly Thr Pro Lys Pro Lys Ser
        35                  40                  45

Gln Thr Glu Gly Asp Phe Glu Glu Ile Pro Asp Glu Asp Ile Leu Asn
    50                  55                  60
```

(2) INFORMATION FOR SEQ ID NO:5:

(i) SEQUENCE CHARACTERISTICS:
        (A) LENGTH: 64 amino acids
        (B) TYPE: amino acid
        (C) STRANDEDNESS: single
        (D) TOPOLOGY: linear     (ii) MOLECULE TYPE: peptide     (vi) ORIGINAL SOURCE:
        (A) ORGANISM: Hirudunaria manillensis     (xi) SEQUENCE DESCRIPTION: SEQ ID NO:5:

```
Val Ser Tyr Thr Asp Cys Thr Glu Ser Gly Gln Asn Tyr Cys Leu Cys
1               5                   10                  15

Val Gly Ser Asn Val Cys Gly Glu Gly Lys Asn Cys Gln Leu Ser Ser
            20                  25                  30
```

-continued

```
Ser Gly Asn Gln Cys Val His Gly Glu Gly Thr Pro Lys Pro Lys Ser
        35                      40                  45

Gln Thr Glu Gly Asp Phe Glu Glu Ile Pro Asp Glu Asp Ile Leu Asn
    50                  55                  60
```

ANTI-HIRUDIN POLYCLONAL ANTIBODIES AND THEIR USE FOR THE IDENTIFICATION, IMMUNOPURIFICATION AND QUANTITATIVE DETERMINATION OF HIRUDIN

This application is a continuation of application Ser. No. 08/205,764 filed Mar. 4, 1994, now abandoned which is a continuation of application Ser. No. 07/903,797, filed Jun. 24, 1992, now abandoned.

The invention relates to a method of producing an antibody specific for a hirudin or a hirudin-like protein.

Hirudin is a polypeptide which may be isolated in small quantities from the salivary glands of the leech *Hirudo medicinalis* (Markwardt F: Untersuchungern uber Hirudin. Naturwissenschaften 41: 537–538, 1955).

Hirudin is a potent and specific inhibitor of thrombin (Chang J Y.: The functional domain of hirudin, a thrombin-specific inhibitor. FEBS Lett. 164: 307–313, 1983). Hirudin binds to thrombin, inhibiting the transformation of soluble fibrinogen into insoluble fibrin and preventing the thrombin mediated activation of factors V, VIII and XIII (Markwardt F.: Pharmacology of hirudin: One hundred years after the first report of the anticoagulant agent in the medicinal leeches. Biomed. Biochem. Acta 44: 1007–1013, 1985).

Thrombin has a greater affinity for hirudin than for the platelet thrombin receptors (Fenton II J W, Landis B. H., Walz D. A., Bing D. H., Feinman R. D., Zabinski M. P., Sonder S. A., Berliner L. J., and Finlayson J. S.: Human thrombin: Preparative evaluation, structural properties and enzymic specificity. In: DH Bind. Ed.: The Chemistry and Physiology of Human Plasma, Pergamon Press, New York, pp. 151–182, 1979) and hence hirudin is able to induce the dissociation of the thrombin-platelet receptor complex (Tam S. W., Fenton J. W. and Detwiler T. C.; Dissociation of thrombin from platelets by hirudin: Evidence for receptor processing. J. Biol. Chem., 254: 8723–8725, 1979), thereby inhibiting the release reaction and platelet aggregation (Hoffmann A., and Markwardt F.: Inhibition of the thrombin-platelet reaction by hirudin. Hemostasis, 14: 164–169, 1984, Reinhold D. S. and Gershman H. Hirudin insensitives thrombin-stimulated platelet release. Thromb. Res., 37: 513–527, 1985).

With a similar mechanism hirudin interferes with the binding of thrombin to the receptors present on endothelial cells and on fibroblasts (Fenton II J. W., Landis B. H., Walz D. A., Bing D. H., Feinman R. D., Zabinski M. P., Sonder S. A., Berliner L. J. and Finlayson J. S.: Human thrombin: Preparative evaluation, structural properties and enzymic specificity. In: DH Bind. Ed.: The Chemistry and Physiology of Human Plasma, Pergamon Press, New-York, pp. 151–182, 1979).

Hirudin also inhibits interaction between thrombin and thrombomodulin, which binds to a common site on thrombin, distinct from the catalytic site (Holfsteenge J., Taguechi H. and Stone S. R.: Effect of thrombomodulin on the kinetics of the interaction of thrombin with substrates and inhibitors. Biochem. J. 237:243–251, 1986).

Hirudin therefore reduces the capacity of thrombin to activate protein C, a serine-protease able to inactivate factors V and VIII, necessary for the generation of thrombin itself.

Hirudin is also able to inhibit clot-bound thrombin which is protected from inhibition by the heparin-antithrombin III complex (Weitz II., Hudoba M., Massel D., Maraganore J. and Hirsh J.: Clot-bound thrombin is protected from inhibition by heparin-antithrombin III but is susceptible to inactivation by antithrombin III independent inhibitors. J. Clin. Invest., 86: 385–391, 1990).

In experimental studies in animals, hirudin proved to be effective in preventing venous and arterial thrombosis (Markwardt F.: Development of hirudin as an antithrombotic Agent. Seminars in Thrombosis and Haemostasis, 15 (3): 269–282, 1989; Heras M., Chesebro J. H., Webster M., Mruk J. S., Grill D. E., Penny W. J., Bowied E. J. W., Badimon L. and Fuster V.: Hirudin, Heparin and Placebo during arterial injury in the Pig. The in vivo role of Thrombin in Platelet. Mediated Thrombosis. Circulation 82: 1476–1484, 1990), vascular shunt occlusions (Kelly A. R., Marzek U. M., Krupski L., Bass A., Cadroy Y., Hauson S. R., and Harker L. A.: Hirudin Interruption of Heparin-Resistant Arterial Thrombus Formation in Baboons. Blood, 77 (5): 1006–1012, 1991) and thrombin-induced disseminated intravascular coagulation (Markwardt F., Howak H. and Hoffman J.: The influence of drugs on disseminated intravascular coagulation DIC. Effects of naturally occurring and synthetic thrombin inhibitors. Thromb. Res. 11: 275–283, 1977).

Although the clinical application of hirudin as an antithrombotic drug was proposed several years ago, this has been severely limited because natural hirudin is not easily available. Nowadays, with genetic engineering methodology and methods of polypeptide purification available, it is possible to produce sufficient amounts of hirudin for preclinical and clinical studies. This fact has renewed interest in natural thrombin inhibitors.

The purification and characterization of different hirudins from the leech *Hirudo medicinalis* was studied in detail and the primary structures of these compounds were determined (Tripier D.: Hirudin, A family of iso-proteins, isolation and sequence determination of new hirudins. Folia Hematol. (Leipz) 115:30–35, 1988). In particular, a form of hirudin designated HV1 was extracted from the whole body of the leech (Boskova I. P., Cherkesova D. V. and Mosolow V. V.: Hirudin from leech heads and whole leechs and pseudo-hirudin from leech bodies. Thromb. Res. 30:459–467, 1983; Dodt J. P., Muller H. P., Seemuller V. and Chang J. Y.: The complete amino acid sequence of hirudin, a thrombin-specific inhibitor. FEBS Lett. 165:180–183, 1984) whereas from the head another form was extracted with a slightly different amino acid sequence, designated HV2 (Harvey R. P., Degryse E., Stefani L., Schamber F., Cazenave J. P., Courtney M., Ialstoshev P. and Lecocq J. P.: Cloning and expression of cDNA coding for the anticoagulant hirudin from the blood sucking leech, *Hirudo Medicinalis*, Proc. Natl. Acad. Sci USA 83:1084–1088, 1986). A third variant designated HV3 has been described (Harvey et al, Proc Natl. Acad. Sci. USA (1986) 1084–1088).

The amino acid sequences of HV1, HV2 and HV3 are SEQ ID Nos. 1, 2 and 3. HV1 and HV2 consist of a single polypeptide chain of 65 amino acids in which the $NH_2$-terminal apolar core and the strongly acid c-terminal tail bind to the apolar binding site and to the anion binding exosite of thrombin, thus preventing it from interaction with the substrate (fibrinogen) (Rydel T. J., Ravichandran K. G., Tulinsky A., Bode W., Huber R., Roitsch C. and Fenton II J. W.: The Structure of a Complex of Recombinant Hirudin and Human α-Thrombin. Science, 249:277–280, 1990). In addition, in position 63 a sulfated tyrosine is present; this post-translational modification does not appear to be essential for antithrombin activity (Stone S. R. and Hofsteenge J.: Kinetics of the inhibition of thrombin by hirudin. Biochem., 25: 4622–4628, 1986).

HV3 is identical to HV2 from positions 1 to 32 and then differs from HV1 in the following respects: Gln at position 33 instead of Asp, Lys at position 35 instead of Glu, Asp at position 36 instead of Lys, Gln at position 53 instead of Asp, Pro at position 58 instead of Glu, Asp at position 62 instead of Glu, Ala at position 63 instead of Tyr (SO$_3$H), Asp at position 64 instead of Leu and Glu at position 65 instead of Gln.

The N-terminal domain (residues 1 to 39) of hirudin is characterized by three disulfide bonds which stabilize the entire conformation (Chang J. Y.: Production, Properties and Thrombin Inhibitory Mechanism of Hirudin Amino-terminal Core Fragments. J. Biol. Chem., 265 (36): 22159–22166, 1990).

Recently, hirudins have also been detected in other species of leeches. In particular, two polypeptides with antithrombin properties similar to those of hirudin HV1 and having the amino acid sequences depicted in SEQ ID NOs 4 and 5 (referred to hereinafter as P1 and P2) were isolated from the leech *Hirudinaria manillensis*, characterized and produced by genetic engineering (European Application No. 92301721.4). P1 shows 60% homology with hirudin HV1 and does not possess sulfated amino acids.

The isolation and purification of hirudin from natural sources or from recombinant biological material is generally carried out by ion exchange chromatography followed by a series of separations through high pressure liquid chromatography (HPLC) on reverse phase columns and on ion exchange columns (Courtney M., Loison G., Lemoine Y., Riehl-Bellon N., Degryse E., Brown S. W., Cazenave J. P., Defreyn G., Delebassee D., Bernat A., Maffrand J. P. and Roitschl.: Seminars in Thrombosis and Haemostasis, 15(3): 288–292, 1989).

Natural and synthetic genes coding for hirudins have been expressed in *Escherichia coli* and in yeast (Harvey R. P., Degryse E., Stefani L., Schamber F., Cazenave J. P., Courtney M., Ialstoshev P. and Lecocq J. P.: Cloning and expression of cDNA coding for the anticoagulant hirudin from the blood sucking leech, *Hirudo medicinalis*, Proc. Natl. Acad. Sci USA 83:1084–1088, 1986; Bergmann C., Dodt., Kohler S., Fink E. and Cjassen H. J.: Chemical synthesis and expression of a gene coding for hirudin, the thrombin-specific inhibitor from the leech *Hirudo medicinalis*. Biol.-Chem. Hoppe Seyler, 367:731–740, 1986; Fortkamp E., Rieger M., Heisterberg-Moutses G., Schweizer S., and Sonnmer R.: Cloning and expression in *Escherichia coli* of a synthetic DNA for hirudin, the blood coagulation inhibitor in the leech. DNA, 5:511–517, 1986).

The resulting unsulfated proteins show biochemical and biological properties very similar to the natural proteins (Talbot M.: Biology of Recombinant Hirudin (CGP 39393): A New Prospect in the treatment of Thrombosis. Seminars in Thrombosis and Haemostasis, 15 (3): 293–301, 1989; Courney M., Loison G., Lemoine Y., Riehl-Bellon N., Degryse E., Brown S. W., Cazenave J. P., Defreyn G., Delebassee D., Bernat A., Maffrand J. P. and Roitschl.: Seminars in Thrombosis and Haemostasis, 15 (3): 288–292, 1989).

With the recombinant proteins it was possible to carry out more extensive preclinical and clinical studies which indicate a low toxicity and immunogenicity of the protein.

The in vivo anticoagulant efficacy of hirudin depends mainly on the maintenance and control of proper levels in the blood. The knowledge of its pharmacokinetics is hence an essential prerequisite for its use as an antithrombotic agent in human. In the course of preliminary studies, Markwardt et al. were able to measure hirudin in biological samples exclusively on the basis of its antithrombin activity assessed in a coagulation test (Markwardt F., Nowak G., Sturzebecher J., Griessbach V., Walsmann P. and Vogal G.: Pharmacokinetics and anticoagulant effect of hirudin in man, Throm. Hemost. 52:160–163, 1984) or using a thrombin-specific chromogenic substrate (Griessbach V., Sturzebecher J. and Markwardt F.: Assay of hirudin in plasma using a chromogenic thrombin substrate. Thromb. Res. 37:347–350, 1985).

Because of the very low immunogenicity of hirudin, it is extremely difficult to raise precipitating antibodies in experimental animals (Bicher J., Germmerli R. and First H.: Studies for revealing a possible sensitization to hirudin after repeated intravenous injections in baboons. Thromb. Res., 61:39–51, 1991).

After various attempts, Spinner et al. (Spinner S., Stoffler G. and Fink E.: Quantitative Enzyme—Linked Immunosorbent Assay (ELISA) for Hirudin. J. Immunol. Methods, 87:79–83, 1986) were able to obtain antibodies, using natural hirudin, in 2 out of 11 immunized goats. These antibodies enabled the development of an ELISA method for the determination of natural and recombinant hirudin.

Recently, monoclonal antibodies were obtained directed against recombinant hirudin (HV1 variant) and against synthetic peptides representing the c-terminal sequence of HV1 (Schlaeppi J. M., Vekemans J., Rink H. and Chang J. Y.: Preparation of monoclonal antibodies to hirudin and hirudin peptides. Eur. J. Biochem., 188:463–470, 1990; Mao S. J. T., Yates M. T., Owen T. J. and Krstenansky J. L.: Preparation of antibodies to a synthetic C-terminus of Hirudin and identification of an antigenic site. J. Immunol. Methods 120: 45–50, 1989). These antibodies were especially used to identify the regions of hirudin involved in the interaction with thrombin. However, their low or even absent reactivity with natural or recombinant hirudin may limit their use in pharmacokinetic studies.

The immunopurification and characterization of the different forms of hirudin has never been performed since specific antibodies are not available in sufficient amounts. The development of immunological methods for the identification, purification and quantitative determination of hirudins and hirudin-like proteins has been until now hindered by the extremely low immunogenicity of these compounds.

Thus, the present invention seeks to provide an effective immunogen capable of reliably raising antibodies against a hirudin or a hirudin-like protein in an experimental animal. The invention further seeks to provide a reproducible method of producing antibodies specific for a hirudin or a hirudin-like protein.

Accordingly, the invention provides a method of producing an immunogen, which method comprises a polymerising a hirudin and/or a hirudin-like protein. The invention also provides an immunogen comprising a polymerised hirudin and/or hirudin-like protein. The invention further provides a method of producing an antibody capable of binding to a hirudin or hirudin-like protein, said method comprising raising antibody against such an immunogen.

The term "a hirudin" as used in herein includes any protein having the sequence of a naturally occurring hirudin isoform, such as HV1, HV2, HV3, P1 or P2. The term "hirudin-like protein" includes any derivative of a hirudin, e.g. by way of amino acid substitution, deletion, insertion, extension, functionalisation or chemical modification, said derivative having anti-thrombin activity. The term "hirudin-like protein" also includes hybrids of more than one hirudin, which may be produced by genetic engineering. For example, WO-A-91/17250 describes a hirudin-like protein composed of the first 46 residues of HV1 followed by amino acids 47 to 65 of HV2.

A hirudin-like protein may be a derivative of HV1, HV2, HV3, P1 or P2 by way of amino acid substitution, deletion, insertion, extension, functionalisation or chemical modification, said derivative having anti-thrombin activity. A substitution, deletion, insertion or extension may comprise one or more amino acid(s). Typically there is a degree of homology of 60% or more between the amino acid sequence of HV1, HV2, HV3, P1 or P2 and the amino acid sequence of the derivative thereof. The degree of homology may be 75% or more, 85% or more, or 95% or more.

The physicochemical character of the original sequence can be preserved, i.e. in terms of charge density, hydrophobicity/hydrophilicity, size and configuration. Candidate substitutions are, based on the one-letter code (Eur. J. Biochem. 138, 9–37, 1984):

A for G and vice versa,

V by A, L or G;

K by R;

S by T and vice versa;

E for D and vice versa; and

Q by N and vice versa.

As far as extensions are concerned, a short sequence of up to 50 amino acid residues may be provided at either or each terminal. The sequence may have up to 30, for example up to 20 or up to 10 amino acid residues.

The hirudin or hirudin-like protein may be subjected to one or more chemical modification(s) (e.g. by post-translational modification), such as glycosylation, sulphation, COOH-amidation or acylation. The Tyr residue at position 63, for example, may be sulphated. A recombinant hirudin or hirudin-like polypeptide would not normally be sulphated at this position. Further, the invention may be applied to lower molecular weight derivatives which do not have the N-terminal or C-terminal portions of HV1, HV2 HV3, P1 or P2.

The immunogen of the invention is a polymer of a hirudin and/or a hirudin-like protein. Thus, the immunogen may be a homopolymer of a hirudin, a homopolymer of a hirudin-like protein or a copolymer of a hirudin and a hirudin-like protein. The immunogen may also be a copolymer of more than one hirudin isoform or more than one hirudin-like protein.

The hirudin and/or the hirudin-like protein are/is suitably polymerised with glutaraldehyde. A molar excess of glutaraldehyde is suitably used. A 1.1 to 5-fold molar excess can be employed.

The polymerization reaction is carried out in the presence of an aqueous solvent. Suitable solvents include phosphate-buffered saline (PBS). The time duration of the reaction is suitably 5 h to 30 h, preferably 15 h to 20 h. The temperature of the reaction is suitably 15° C. to 35° C., for example from ambient temperature to 30° C. From the viewpoint of convenience, ambient temperature is preferred.

Methods for obtaining the hirudin and/or the hirudin-like starting material are known. These methods include extraction of hirudins from leeches and production of recombinant hirudins and hirudin-like proteins by genetic engineering. Hirudins and hirudin-like proteins, particularly HV1, HV2, HV3 and derivatives thereof, may be obtained in a accordance with WO-A-91/17250. The method of WO-A-91/17250 is based on chemical synthesis of a nucleotide sequence encoding a hirudin or a hirudin-like polypeptide, and expressing the polypeptide in a recombinant organism. P1 and P2 may be isolated from tissue of the leech *Hirudo manillensis* by obtaining a preparation according to WO-A-90/05143 (U.S. Ser. No. 07/721,536) and subjecting the preparation to high pressure liquid chromatography (European Application No. 92301721.4, U.S. Ser. No. 07/842,089).

The invention provides a method for producing an antibody capable of binding to a hirudin or a hirudin-like protein, said method comprising raising antibodies against an immunogen according to the invention. The antibody produced may be monoclonal or polyclonal.

Methods of producing monoclonal and polyclonal antibodies are well known. A method for producing a polyclonal antibody comprises immunising a suitable host animal, for example an experimental animal, with an immunogen of the invention and isolating immunoglobulins from the serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein, Nature 256, 495–497, 1975).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunoisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen of the invention may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

The invention includes a method for the quantitative determination, purification or identification of a hirudin or a hirudin-like protein said method comprising raising antibodies against an immunogen according to the invention and using the antibody thereby obtained in said quantitative determination, purification or identification.

Conventional methods for the quantitative determination of an antigen in a sample using an antibody may be used. For example, an antibody produced in accordance with the invention may be used in an ELISA (enzyme-linked immunoassay) method such as a non-competitive ELISA.

Typically, an ELISA method comprises the steps of (i) immobilising on a solid support an unlabelled antibody produced in accordance with the invention, (ii) adding a sample containing the hirudin and/or hirudin-like protein to be determined such that the hirudin and/or hirudin-like protein is captured by the unlabelled antibody, (iii) adding an antibody produced in accordance with the invention which has bee labelled, and (iv) determining the amount of bound labelled antibody.

Examples of suitable antibody labels include biotin (which may be detected by avidin conjugated to peroxidase) and alkaline phosphatase. The sample containing the hirudin and/or hirudin-like proteins may be biological fluid (e.g. a leech extract), tissue culture medium from a culture of either non-transferred or transformed cells, or a sample produced by recombinant DNA procedures.

Conventional methods of purifying an antigen using an antibody may be used. Such methods include immunoprecipitation and immunoaffinity column methods. In an immunoaffinity column method, an antibody produced in accordance with the invention is coupled to the inert matrix of the column and a sample containing the hirudin and/or hirudin-like protein to be purified is passed down the column, such that the hirudin and/or hirudin-like protein is retained. The hirudin and/or hirudin-like protein is then eluted.

The sample containing the hirudin or hirudin-like protein may be biological fluid (e.g. leech extract) tissue culture medium from a culture of transformed or non-transformed cells, or a sample produced by recombinant DNA procedures.

Conventional methods for identifying an antigen with an antibody may be used. For example, a Western blotting method may be used. Such a method can comprise the steps of
  (i) subjecting a sample containing a hirudin and/or a hirudin-like protein to gel electrophoresis,
  (ii) transferring the separated proteins in the gel onto a solid support (e.g. a nitrocellulose support) by blotting, and
  (iii) allowing an antibody produced in accordance with the invention and which has been labelled to bind to the hirudin and/or hirudin-like protein.

The sample containing the hirudin and/or hirudin-like protein may be biological fluid, (e.g. leech extract), tissue culture medium from a culture of transformed or non-transformed cells, or a sample produced as a result of recombinant DNA procedures.

The following Examples illustrate but do not in any way limit the invention. In the accompanying drawings.

EXAMPLE 1

Procedure for making the Antigen Immunogenic

HV1 hirudin, obtained in *Escherichia coli* by recombinant DNA technology, was dissolved at a concentration of 6 mg/ml in PBS pH 7.3 containing 1.25% glutaraldehyde and incubated for 18 hours at room temperature. After dialysis against 0.9% NaCl the formation of hirudin polymers was checked by 15% polyacrylamide gel electrophoresis (SDS-PAGE).

Figure 1:
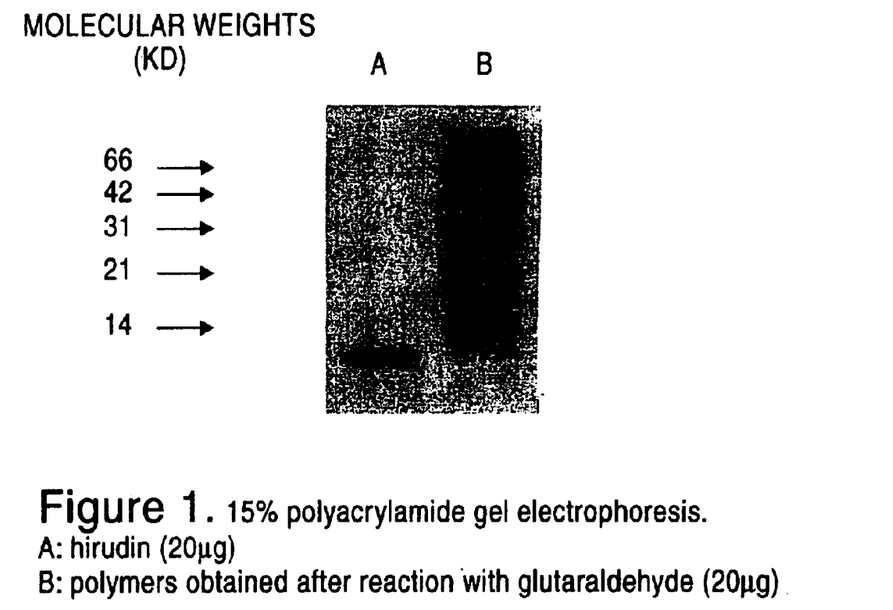
FIG. 1 shows a sodium dodecyl sulfate polyacrylamide electrophoresis (SDS-PAGE) gel of hirudin HV1 polymers obtained after reaction of HV1 and glutaraldehyde. Lane A is loaded with hirudin (20 µg) and lane B is loaded with the HV1 polymers (20 µg). The numbers on the left of the gel are molecular weights (kD).

FIG. 1 shows the polymers formed after the reaction. The band corresponding to hirudin (A) disappears whereas 7 compounds (B) appear with molecular weights corresponding to multiples of that of the starting hirudin.

With a similar procedure it is possible to prepare immunogenic polymers of other forms of hirudin, for example HV2 and P1.

EXAMPLE 2

Induction and Isolation of the Antibody

5 New Zealand white, male rabbits were inoculated subcutaneously with 250 µg of HV1 hirudin polymer re-suspended in 2 ml of Freund's complete adjuvant. Booster injections with Freund's incomplete adjuvant were give after 4, 6, 8 and 10 weeks. At week 12, 30 ml of blood were taken from each animal and the presence of precipitating antibodies was determined by the double diffusion technique in agarose gel according to Outcherlony (Outcherlony O.: Diffusion in gel methods for immunological analysis. Progr. Allergy, 5.1, 1958). Five wells were obtained form a 1% agarose gel in 0.15 M PBS pH 7.4 as shown in FIG. 2.

35 µl of immune serum diluted 1:16 in PBS was loaded in well A, whereas in wells B, C, D, E, buffer, 2.5, 5 and 10 µg of HV1 hirudin, respectively were loaded. After 48 hours incubation at room temperature in a moist chamber the gel was washed for 24 hours with normal saline and distilled water, dried at 40° C. and stained with Coomassie blue 0.2% in 50% trichloroacetic acid.

Figure 2:
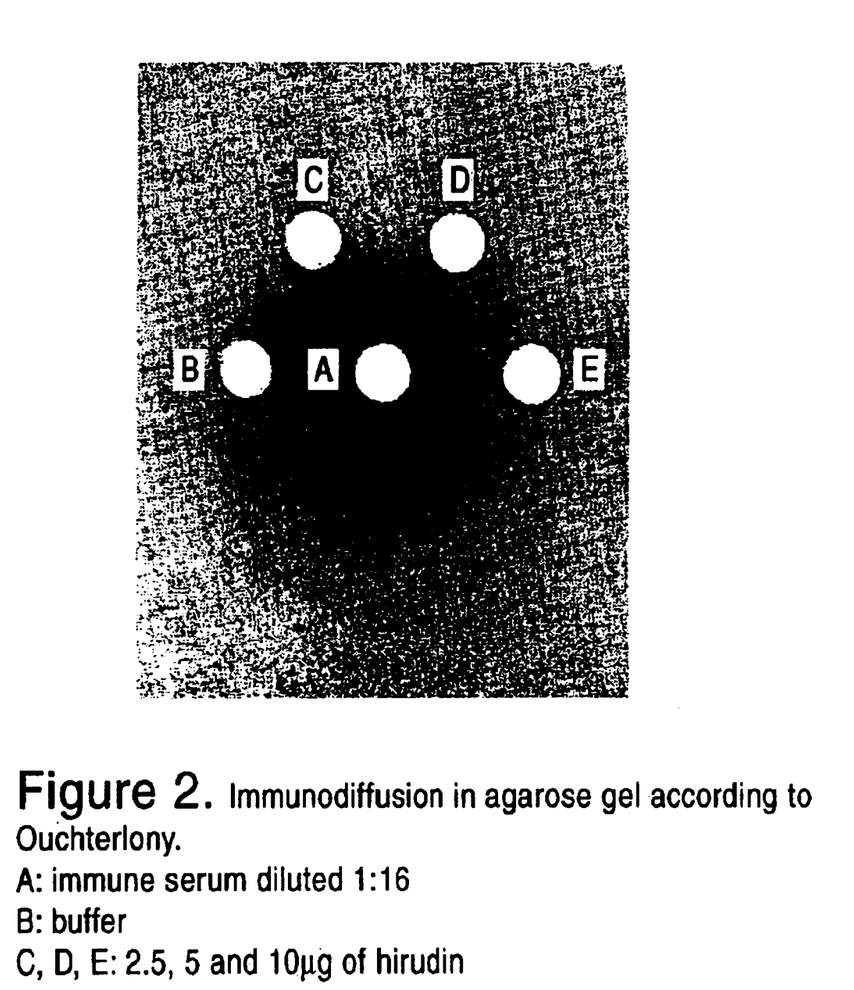
FIG. 2 shows an immunodiffusion agarose gel according to Ouchterlony. Well A contains immune serum diluted 1:16, well B contains buffer, and wells C, D and E contain 2.5, 5 and 10 µg of hirudin respectively. The gel demonstrates the presence of precipitating antibodies in blood obtained form inoculated rabbits.

FIG. 2 shows well-defined precipitation bands between the central well A and wells C, D, E in which hirudin was placed.

In a parallel experiment in which non immune rabbit serum was placed in well A, no precipitation bands were observed, whereas in this experiment four out of the 5 immunized rabbits showed the pressure of precipitating antibodies.

The IgG fraction was prepared by protein A-sepharose chromatography, serum diluted 1:2 in PBS pH 7.4 was loaded on a protein A-sepharose column equilibrated with PBS pH 7.4. The IgG were subsequently eluted with 0.1 M citrate buffer pH 3. Using a similar procedure it is possible to prepare polyclonal antibodies for other forms of hirudin, for example HV2 and P1.

EXAMPLE 3

Immunoenzymatic Determination of the Antigen using the ELSIA Method.

A part of the anti HV1 IgG isolated in Example 2 was biotinylated according to the method of Guesdon et al (Guesdon J. L. et al.: The use of avidin-biotin interaction in immunoenzymatic techniques. J. Histochem. Cytochem., 27: 1131–1139, 1975).

The following scheme was followed for the ELISA test. Rabbit polyclonal anti HV1 IgG were immobilized in the solid phase for capturing the antigen (HV1) contained in the samples which was then tagged with rabbit polyclonal biotinylated IgG anti HV1. Detection was carried out with avidin conjugated to peroxidase. More precisely: 150 µl of polyclonal IgG, 10 µl/ml in 0.1 M $Na_2CO_3$ pH 9.6 were placed in microplate wells and incubated for 16 hours at 4° C. The concentration of IgG was chosen so as to optimize ELISA and obtain high sensitivity and low background.

The plates were washed and the remaining binding sites blocked by incubation for one hour with PBS pH 7.4 containing 3% bovine albumin. After washing, the plates were incubated for 60 minutes at 37° C. either with PBS-Tween pH 7.4 or with plasma or urine, containing increasing concentrations of standard hirudin or samples at unknown concentrations. After washing with PBS-Tween pH 7.4 the plates were incubated for 60 minutes at 37° C. with 5 µg/ml of biotinylated IgG, washed again and incubated for 60 minutes at 37° C. with 158 ng/ml of avidin-peroxidase. The plates were then washed three times with PBS-Tween pH 7.4 and once with bidistilled water. Peroxidase was allowed to react for 15 minutes at room temperature with 0.1% o-phenylendiamine, 0.015% $H_2O_2$ in 0.1 M citrate buffer pH 5. The reaction was stopped by adding 4.5 M $H_2SO_4$ and absorbence was measured at 490 nm by a microplate reader.

Figure 3:
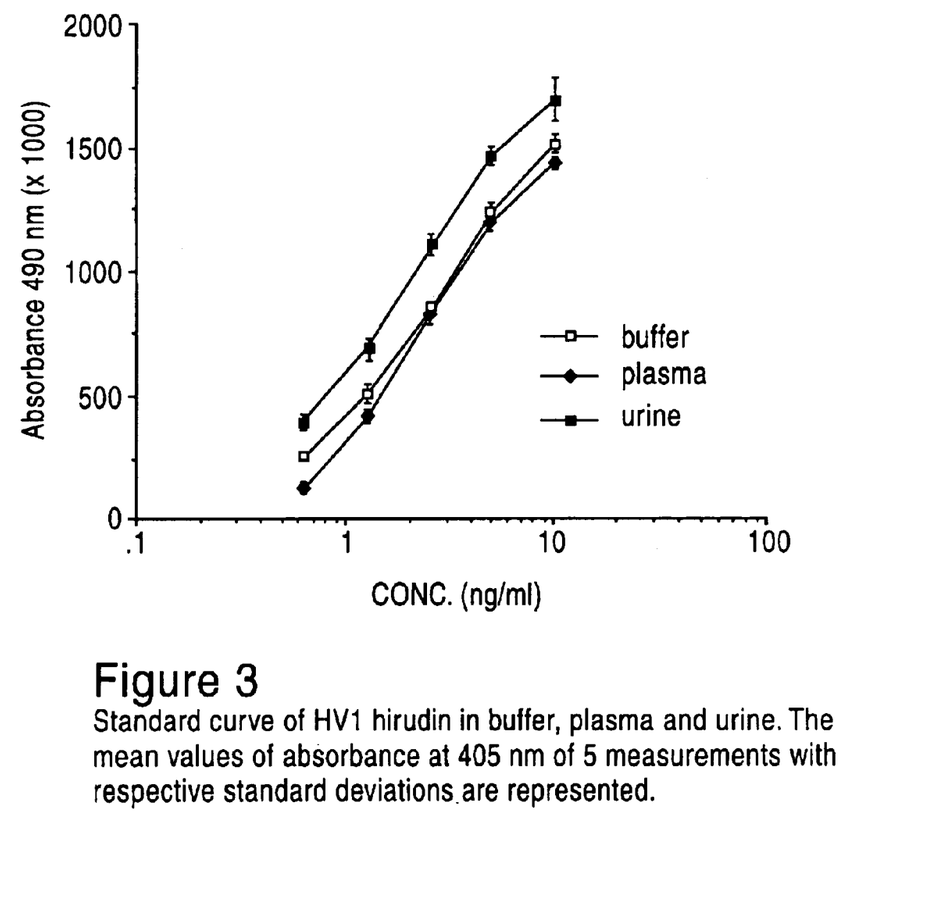
FIG. 3 shows a standard curve for HV1 hirudin of absorbence at 490 nm (x1000) (x-axis) versus concentration of hirudin (ng/ml) in buffer (—□—), plasma (—◆—) and urine (—■—) (y-axis). Each point on the curve represents the mean of five measurements of absorbance at 490 nm and the bars represent standard deviations.

A dose-dependent linear relationship was obtained between 0.61 and 10 ng/ml with a limit of detection of 0.3 ng/ml (FIG. 3). The coefficient of variation between the dosages was established on the basis of 7 different doses and ranged between 3.89% and 6.28%.

Figure 4:
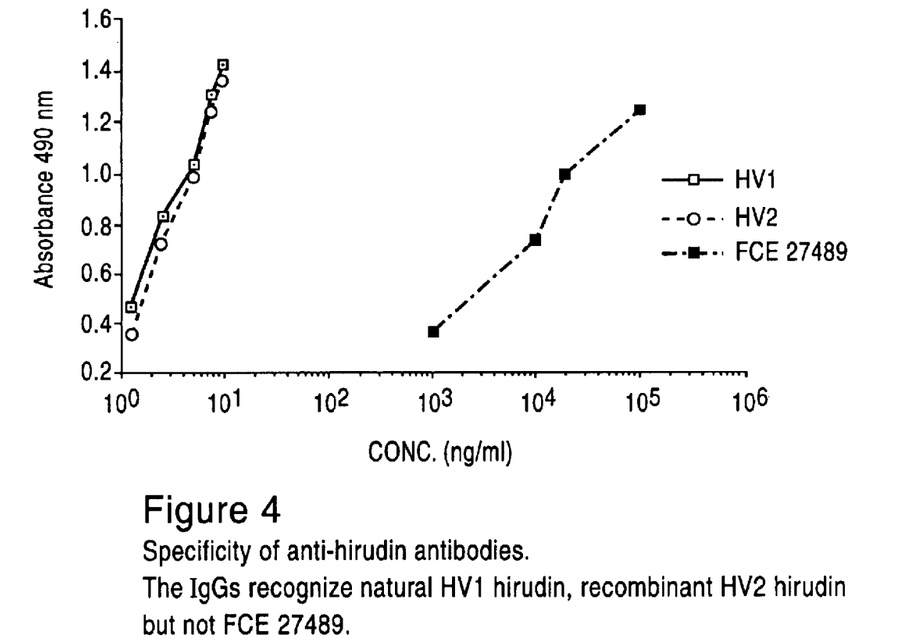
FIG. 4 shows the specificity of the anti-hirudin antibodies obtained in Example 2 for natural HV1 (—□—) and recombinant HV2 (---○---) but not P1 (---■---). The x-axis is concentration of hirudin (ng/ml) and the y-axis is absorbance at 490 nm.

The specificity of the anti HV1 antibodies isolated in Example 2 was tested by ELISA against natural HV1 hirudin, recombinant HV2 hirudin and P1 (FIG. 4).

The antibodies recognize natural HV1 hirudin and the HV2 variant but not P1 which shows 60% homology with HV1 hirudin. Antibodies able to recognize hirudins, in particular P1, can be obtained, as already said, by a procedure similar to that described in Example 2 and used, for example in an ELISA method similar to that described in Example 3, for the determination of hirudins, in particular P1.

What is claimed is:

1. An immunogen consisting essentially of a set of hirudin polymers being devoid of any heterologous carrier protein and having sufficient immunogenicity, in the absence of conjugation to said carrier protein, to elicit an antibody which binds specifically to a natural or recombinant hirudin, and, the majority of said polymers having at least three monomer units, said monomers selected from the group consisting of HV1 (SEQ ID NO:1), HV2 (SEQ ID NO:2), and HV3 (SEQ ID NO:3).

2. An immunogenic composition for administering to a host consisting essentially of the immunogen according to claim 1, and an adjuvant.

3. A method of making the immunogen according to claim 1, consisting essentially of polymerizing said monomers of hirudin under conditions such that a majority of polymers formed have at least 3 monomer units, said conditions including a molar excess of cross-linking agent relative to said monomers, and an absence of carrier protein.

4. The method according to claim 3, wherein said cross-linking agent is glutaraldehyde.

5. The method according to claim 4, wherein said glutaraldehyde is present in 1.1 to 1.5 molar excess.

* * * * *